United States Patent [19]

Myers, Jr. et al.

[11] Patent Number: 5,298,430
[45] Date of Patent: Mar. 29, 1994

[54] IMMUNOASSAY PROCESS UTILIZING A CELLULOSE ORGANIC ESTER FIBRET SUPPORT ELEMENT

[75] Inventors: Thomas J. Myers, Jr., Charlotte; Lessie C. Phillips, Huntersville, both of N.C.

[73] Assignee: Hoechst Celanese Corporation, Somerville, N.J.

[21] Appl. No.: 243,746

[22] Filed: Sep. 13, 1988

[51] Int. Cl.$^5$ .................. G01N 33/544; C12N 11/12; C12N 11/08; C12M 1/00
[52] U.S. Cl. .................................. 436/530; 435/179; 435/181; 435/287; 435/311; 435/967
[58] Field of Search .................. 424/12; 435/7, 179, 435/181, 287, 311, 967; 436/530

[56] References Cited
U.S. PATENT DOCUMENTS 4,357,311  11/1982  Schutt ................................. 424/12

OTHER PUBLICATIONS

Fisher Scientific Catalog, 1986, pp. 710, 712, 714.

*Primary Examiner*—Margaret Moskowitz
*Assistant Examiner*—Bradley L. Sisson
*Attorney, Agent, or Firm*—R. H. Hammer, III

[57] ABSTRACT

Immunoassay process for the detection of an antigen in a sample of blood, serum, urine and other liquids employing a test apparatus comprising a reaction chamber and a support element in the reaction chamber comprising a blend of from about 5 to 95 percent cellulose organic ester fibrets and from about 95 to 5 percent by weight of a dispersible cut fibers where a predetermined amount of an antibody capable of extracting an antigen from the sample is bound to the support element, the process comprising depositing the sample on the upper surface of the support element and detecting the amount of antigen in the sample.

8 Claims, 1 Drawing Sheet

IMMUNOASSAY PROCESS UTILIZING A CELLULOSE ORGANIC ESTER FIBRET SUPPORT ELEMENT

FIELD OF THE INVENTION

The present invention relates to an immunoassay process for the detection of antigens in a sample of blood, serum, urine and other liquids. More particularly, the invention relates to a immunoassay process which utilizes an improved support element comprising a blend of cellulose organic fibrets and dispersible cut fibers.

BACKGROUND OF THE INVENTION

Various immunoassay test methods and apparatus are known in the art. Typical test apparatus such as the one described in U.S. Pat. No. 4,623,901, use a multilayer construction to perform varying functions, for example, a first layer serves to entrap particles such as the antibody specific to the immunoassay technique, a second layer controls the flow of the liquid through the test apparatus and a third layer provides an absorbent for the liquid sample at the bottom of the kit. This multilayer construction, however, increases the number of steps of the process, increases the size of the kit and also increases the number of manufacturing steps required to assemble the kit.

These multilayers are typically made of fibers of nylon, glass, polyester, polyolefins and cellulose acetate. Fibrets of cellulose organic esters, however, heretofore have not been combined with dispersible cut fibers to form filter materials in general, and specifically have not been combined to form a support element used in an immunoassay process. Fibrets of cellulose organic esters and particularly cellulose acetate have been used for lightweight paper products such as those adaptable for uses as tobacco smoke filters, industrial air filters and filters for organic compounds.

SUMMARY OF THE INVENTION

With this in mind, the present invention provides an immunoassay process for the detection of antigens in a sample of blood, serum, urine and other liquids. This process utilizes an apparatus comprising a reaction chamber and a support element therein where the support element comprises a blend of from about 5 to 95 by weight percent cellulose organic ester and from about 95 to 5 percent by weight of dispersible cut fibers. A pre-determined amount of an antibody capable of extracting an antigen from the sample is bound to the support element. The process comprises depositing the sample and reagents on the upper surface of the support element and detecting the amount of antigen in the sample. Such a process eliminates the multilayer constructions of the prior art in that the support element of the present invention can perform all the functions and steps thereof in a unitary layer.

DETAILED DESCRIPTION OF THE INVENTION

It has been found in accordance with this invention that a blend of cellulose organic ester fibrets and dispersible cut fibers can be molded into an immunoassay filter element and used in an improved immunoassay process.

Cellulose organic esters are obtained by esterifying cotton linter or wood pulp and are typically, but not limited to, esters of a carboxylic acid having from 1 to about 4 carbon atoms. Exemplary esters may include cellulose formate, cellulose acetate, cellulose butyrate, cellulose acetate butyrate, cellulose propionate, cellulose acetate propionate and cellulose triacetate. Cellulose acetate is a particularly useful cellulose organic ester.

The term "fibrets" is understood by persons skilled in the art as referring to a high surface area, fibrillar material having surface areas in excess of 5 square meters per gram, preferably about 20 square meters per gram, lengths of from about 20–200 microns and diameters of from about 0.5 to 5 microns. Various methods of forming these fibrets are known in the art, and are described for example in U.S. Pat. Nos. 4,047,862, 4,192,838 and 4,283,186.

Suitable dispersal cut fibers include fibers of cellulose organic esters, polyesters, wood pulp, glass, polyamides, polyolefins and polybenzimidazoles. Suitable cut fibers typically have a surface area of less than about 1 square meter per gram, fiber lengths of greater than about 200 microns and not exceeding 25,000 microns, and diameters per fiber of from about 1 to 60 microns. A particularly suitable cut fiber is polyester flock.

The cellulose organic esters fibret alone are not suitable for use as a support element because there is negligible flow of liquid through a filter made solely of fibrets. Cut fibers used alone and without cellulose organic ester fibrets lack sufficient integrity to act as a support element and do not have the necessary pore structure. However, when blended together in amounts of from about 5 to about 95 weight percent of the fibrets and from about 95 to about 5 weight percent of the cut fibers, the resulting blend can be used to form a functional support element.

Figure 1:
FIG. 1 is a scanning electronmicrograph of the exterior surface structure of a support element at 100× magnification.
Figure 2:
FIG. 2 is a scanning electronmicrograph of the exterior surface structure of a support element at 500× magnification.
Figure 3:
FIG. 3 is a scanning electronmicrograph of the exterior surface structure of a support element also at 500× magnification.

Referring to FIGS. 1-3, which are electronmicrographs of a support element comprising a blend of 95 weight percent fiberglass and 5 weight percent cellulose acetate fibrets, the surface structure has a random orientation of the cut fibers in the x-y-z plane and are bound together in all directions by the fibrets. The fibrets provide a web-like and complex pore structure with an infinite number of layers. On a macroscopic level the surface of the support element is substantially smooth and less grittier than conventional filter paper.

In use the cut fibers provide the necessary capillary action to draw or adsorb the sample, whereas the fibrets provide the necessary filtering affect and contribute to the flow rate and flow direction of the sample. Thus, the present support element can perform the varying functions typically performed by multilayer test apparatus constructions.

The support element is prepared by first dispersing the cellulose organic ester fibrets in a liquid dispersion medium such as water or a low molecular weight alcohol. Optionally, the liquid medium can contain a dispersing agent such as a surfactant. The liquid medium will normally contain a ratio of from about 0.5 to 1.5 g dry weight of fibrets to 750 ml of the dispersion medium. Agitation is used to adequately disperse the fibrets therein.

The cut fibers are then also dispersed in the dispersion medium using agitation so as to obtain a concentration of from 95 to 5 weight percent of the cut fibers in the support element. This forms a slurry and the dispersion medium is removed by use of a vacuum to form a cake having about 20 percent solids. The cake is placed in a compression molding die and the cake is molded into a predetermined shape such as a wafer-shaped disk under a pressure of up to about 20,000 psi. The resulting support element is dried to a water level of less than 1 percent by drying in air for 8 to 12 hours or in an oven at 70° to 100° C. for about one hour.

The surface of the support element is a microporous structure formed by the interaction of the fibrets with the dispersible cut fibers. The flow rate of a liquid placed on the surface is controlled by the composition of the support element, specifically by the ratio of fibrets to dispersible fibers, the alignment of dispersible fibers in the z direction which effects the number of capillaries in the downward direction, and by the final density of the support element as determined by the pressure used in forming the support element.

To increase the flow rate of the liquid through the support element the ratio of fibrets to dispersible fibers is decreased and the alignment of dispersible fibers in the z direction is maximized by reducing the pressure exerted on the element in the forming step. The overall density of the element is also reduced such that micronsized cavities exist to support the increased flow requirement.

To decrease the rate, the fibrets to dispersible fibers ratio is increased as well as the forming pressure and subsequently the final density. The flow profile of the liquid which is the ratio of radial flow to downward flow and is critical to the effectiveness of subsequent wash steps a described in the testing procedure, is most effectively controlled by adjusting the ratio of fibrets to dispersible fibers.

To increase this ratio, that is to cause the liquid to flow more rapidly in the radial direction and slower in the downward direction, the ratio of fibrets to dispersible fibers can be increased at a constant forming pressure. Alternatively, and less desirable due to the resiliency of the dispersible cut fibers, the pressure can be increased while keeping fiber ratios the same. To increase downward flow and reduce radial flow the ratio of fibrets to dispersible fibers can be decreased at a constant forming pressure.

The support element can then be mounted in a reaction chamber made of plastic or other suitable preferably inexpensive and readily disposable material. Typically, the chamber is constricted so as to funnel the liquid sample such as blood, serum or urine onto the support element for testing.

The support element can be used as a filter medium in many different types of immunoassay tests depending on the reagents or antibodies bound to the support element. In particular, the present invention can be used in an immunoassay process which comprises depositing the sample of blood, serum, urine or other liquid to be tested on the upper surface of the support element and permitting such sample to flow through the support element. The amount of antigen in the sample is detected utilizing a known detection technique such as competition-type and sandwich-type assay techniques. These techniques are based on formation of a complex between the antigen contained in the sample being assayed and a labelled antibody o antibodies bound to the support element. The antibodies may be labelled with an isotope, enzyme or fluorescing compound which permits its detection or the quantitative analysis thereof after separation of the complexed labelled antigen or antibody from uncomplexed labelled antigen or antibody.

Specifically, in a competition-type assay, the antigen of the sample competes with a known quantity of labelled antigen for a limited amount of the binding sites of an antibody bound to the support element. The amount of labelled antigen bound to the antibody is inversely proportional to the amount of antigen in the sample.

In a sandwich-type assay, the antibody is bound to a solid phase such as latex microbeads or microparticles having a size of 0.3 to 1.2 microns. These microbead carriers are filtered through the support element so that the microbeads are entrapped by the pore structure on the surface of support element and the antibody is thus bound to the top surface of the support element. The sample being assayed is then contacted with the antibody to extract the antigen therein by formation of an antibody-antigen complex. After an optional incubation period, the support element is washed to remove any residue of the sample and then contacted with a solution containing a known quantity of labelled antibody. The labelled antibody complexes with the antigen bound to the support element through the unlabelled antibody. The support element is washed to remove the unreacted labelled antibody, and the presence of the labelled antibody is determined.

Additionally the support element may include a blocking agent which blocks non-specific binding of the antibody/antigen complex to the support element. Exemplary blocking agents which are known in the art and are described, for example, in Journal of Immunological Methods 101 (1987) pp 43-50 include instantized dry milk, casein, gelatins from pig and fish skin, serum albumin, and other similar proteins. These blocking agents can be incorporated into the support element by adding it directly to the support element or by adding it to the dispersion medium.

By using specific antigens, antibodies and binding substances bound to the support element and different antigen detection techniques, the present process utilizing the present support element can be used for testing blood, serum and urine for the level of antigens or antibodies associated with pregnancy, AIDS, hepatitis, herpes virus, drug use, diabetes, and specific other bacteria, parasites, fungi and viruses.

A specific test procedure is illustrated with the following example which is to be considered as illustrative of the present invention. It should be understood, however, that the invention is not limited to the specific details of the example.

EXAMPLE

A disk was produced by dispersing in water using agitation 7.5 percent by weight of cellulose acetate fibrets. 92.5 percent by weight of polyester flock (cut fibers) were then dispersed in the water to form a cellulose acetate fibret/polyester cut fiber blend. The water was removed by vacuum to form a cake. The cake was molded into a wafer-shaped disk having a diameter of 5.9 cm and a thickness of 0.3 cm. The disk was dried in air overnight.

A monoclonal antibody against human choriogonadotropin (HCG) was bound thereto at a predetermined site. HCG is an antigen which is elevated in the urine of pregnant women. A 100 ul sample of phosphate buffered saline buffer having a concentration of 0.5 M and pH of 7.2 and including 1 percent bovine serum albumin was dropped onto the HCG site. Twenty samples of urine were then deposited on twenty individual disks, 10 of which were known positive for HCG and 10 of which were known negative for HCG. A series of reagents were then dropped on each of the disks in order as follows: 50 ul of anti HCG serum regent (2 percent in the phosphate buffered saline), followed by 45 ul of 1.0 M sodium chloride followed by 6.5 ul of 0.01 percent chromogen. The 10 disks known positive for HCG tested positive and the 10 disks known negative for HCG tested negative.

Although the invention has been described using a assay for HCG as an example, other assays may be constructed and the support element can be utilized in combination with other filtering techniques.

In the specification, there have been disclosed preferred embodiments of the invention and, although specific terms are employed, they are used in a generic and descriptive sense only and not for the purpose of limitation, the scope of the invention being set forth in the following claims.

That which is claimed is:

1. A support element for use in immunoassays comprised of a blend of from about 5 to about 95 percent cellulose organic ester fibrets and from about 95 to about 5 percent by weight of dispersible cut fibers molded and compressed into a predetermined shape.

2. A support element according to claim 1, wherein the cellulose organic ester is selected from the group consisting of cellulose formate, cellulose acetate, cellulose butyrate, cellulose acetate butyrate, cellulose propionate, cellulose acetate propionate and cellulose triacetate.

3. A support element according to claim 1, wherein the cellulose organic ester fibrets are cellulose acetate fibrets.

4. A support element according to claim 1, wherein said dispersible cut fibers are selected from the group consisting of fibers of cellulose organic esters, polyesters, wood pulp, glass, polyamides, polyolefins and polybenzimidazoles.

5. A support element according to claim 1 wherein the predetermined shape is a wafer-shaped disk.

6. A support element for use in immunoassays comprised of a blend of from about 5 to about 10 percent by weight cellulose acetate fibrets and from about 95 to about 90 percent by weight of dispersible cut fibers selected from the group consisting of fibers of cellulose organic esters, polyesters, wood pulp, glass, polyamides, polyolefins and polybenzimidazoles, molded and compressed into a wafer-shaped disk.

7. A method for the preparation of a support element for use in immunoassays comprising the steps of dispersing cellulose organic ester fibrets in a liquid dispersion medium; dispersing cut fibers in the liquid dispersion medium to form a blend; separating the dispersion medium from the cellulose organic ester fibret/cut fiber blend to form a cake; and molding the cake under pressure into a predetermined shape.

8. A method according to claim 7 wherein the cellulose organic fibrets are cellulose acetate fibrets.

* * * * *